(12) United States Patent
Roberts et al.

(10) Patent No.: US 12,320,945 B2
(45) Date of Patent: Jun. 3, 2025

(54) PROBABILISTIC OIL PRODUCTION FORECASTING

(71) Applicant: Schlumberger Technology Corporation, Sugar Land, TX (US)

(72) Inventors: Timothy J. Roberts, Houston, TX (US); Supriya Gupta, Houston, TX (US); Aria Abubakar, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1223 days.

(21) Appl. No.: 16/646,603

(22) PCT Filed: Sep. 13, 2018

(86) PCT No.: PCT/US2018/050882
§ 371 (c)(1),
(2) Date: Mar. 12, 2020

(87) PCT Pub. No.: WO2019/055653
PCT Pub. Date: Mar. 21, 2019

(65) Prior Publication Data
US 2020/0257932 A1 Aug. 13, 2020

Related U.S. Application Data

(60) Provisional application No. 62/558,293, filed on Sep. 13, 2017.

(51) Int. Cl.
*G06F 30/20* (2020.01)
*G01N 33/24* (2006.01)
(Continued)

(52) U.S. Cl.
CPC .......... *G01V 20/00* (2024.01); *G01N 33/241* (2013.01); *G06N 7/01* (2023.01); *G06Q 10/063* (2013.01)

(58) Field of Classification Search
CPC .... G01V 99/00; G01V 99/005; G01N 33/241; G06N 7/01; G06Q 10/04; G06Q 10/063; G06Q 50/02
See application file for complete search history.

(56) References Cited

U.S. PATENT DOCUMENTS

2014/0006111 A1* 1/2014 Priyesh .................. B60R 3/007
705/7.36
2014/0229151 A1* 8/2014 Ranjan .................. E21B 43/00
703/10
(Continued)

FOREIGN PATENT DOCUMENTS

| CA | 2818464 A1 | 12/2013 |
|---|---|---|
| WO | 2015/171799 A1 | 11/2015 |
| WO | 2017/139271 A2 | 8/2017 |

OTHER PUBLICATIONS

Oliver, Dean S., and Yan Chen. "Recent progress on reservoir history matching: a review." Computational Geosciences 15 (2011): 185-221.*

(Continued)

*Primary Examiner* — Nithya J. Moll
(74) *Attorney, Agent, or Firm* — Michael Guthrie; Jeffrey D. Frantz

(57) ABSTRACT

A method includes receiving historical well-production data, and determining curve parameters based on the historical well production data. Determining the curve parameters includes accounting for uncertainty. The method also includes determining curve fits for the historical data based on the curve parameters using a plurality of models, calculating accuracy for each of the models based on a compari- (Continued)

son of the curve fits to the well-production data, comparing the accuracy for each of the models using an information criteria that accounts for uncertainty, selecting one of the models based on the comparison, and determining an estimated ultimate recovery (EUR) for the well using at least the selected one of the models.

18 Claims, 14 Drawing Sheets

(51) Int. Cl.
    *G01V 20/00*     (2024.01)
    *G06N 7/01*     (2023.01)
    *G06Q 10/063*     (2023.01)

(56) References Cited

U.S. PATENT DOCUMENTS

| | | | |
|---|---|---|---|
| 2014/0297235 A1* | 10/2014 | Arora | G06N 7/01 |
| | | | 703/2 |
| 2016/0260181 A1* | 9/2016 | Singh | G06Q 50/02 |
| 2016/0312607 A1 | 10/2016 | McNealy | |

OTHER PUBLICATIONS

Sidahmed, Mohamed, et al. "Enhancing Wellwork Efficiency with Data Mining and Predictive Analytics." SPE Intelligent Energy International Conference and Exhibition. SPE, 2014.*

Mehrjou, Arash, Reshad Hosseini, and Babak Nadjar Araabi. "Improved Bayesian information criterion for mixture model selection." Pattern Recognition Letters 69 (2016): 22-27.*

Minamimoto, Takafumi, et al. "Hydration level is an internal variable for computing motivation to obtain water rewards in monkeys." Experimental brain research 218 (2012): 609-618. (Year: 2012).*

Koller, et al., "Probabilistic Graphical Models: Principles and Techniques," Massachusetts Institute of Technology, The MIT Press, 2009.

International Search Report and Written Opinion for the counterpart International patent application PCT/US2018/050882 mailed on Dec. 10, 2018.

International Preliminary Report on Patentability for the counterpart International patent application PCT/US2018/050882 mailed on Mar. 26, 2020.

Extended Search Report issued in European Patent Application No. 18855396.0 dated May 3, 2021, 6 pages.

Communication pursuant to Article 94(3) EPC issued in the European Patent Application No. 18855396.0 dated Jun. 5, 2024, 11 pages.

Morehouse, D. FL., The Intricate Puzzle of Oil and Gas "Reserves Growth", Energy Information Administration, Natural Gas Monthly, 14 pages.

* cited by examiner

PROBABILISTIC OIL PRODUCTION FORECASTING

CROSS-REFERENCE TO RELATED APPLICATIONS

This application is a National Stage Entry of International Application No. PCT/US2018/050882, filed Sep. 13, 2018, which claims priority to U.S. Provisional Patent Application No. 62/558,293, which was filed on Sep. 13, 2017, and incorporated by reference herein in its entirety.

BACKGROUND

Production forecasting is conducted in oilfield applications for asset performance evaluation and optimization. Decline curve analysis (DCA) is used for production forecasting and determining estimated ultimate recovery (EUR). Financial institutions generally consider DCA estimates for reserves evaluation. When history-matched simulation models are not available, an empirical approach to DCA may be used for estimation of reserves. Further, in the case of a large number of wells, it may not be practical to use numerical modeling, and DCA can provide quick and reliable estimates when applied properly. Assumptions used in some DCA methods include that there is no significant change in operating conditions and field development during the production life of a well, a constant bottomhole flowing pressure, and boundary-dominated flow conditions being true.

Historical production data used for DCA can be sporadic and of low frequency with incorrect and missing measurements. Data quality assurance (QA), quality control (QC), and interpretation are subjective when there is no preprocessing and standard methodology for data treatment. Different engineers may thus interpret data differently and introduce their bias during data preprocessing and removal of outliers. In the absence of a robust algorithm, forecast curves are affected by outliers, thus increasing the uncertainty. Further, decreasing data frequency, may yield increasing effects of outliers on overall fit. In the case of missing data, engineers either interpolate or ignore the missing data. Capturing the trend of production behavior before and after the missing data becomes helpful in determining the next steps, and, many times, that trend is not readily apparent.

After the data are preprocessed, to save time, a single forecasting method is selected and run for all the wells, although another, unused method could better fit the data. Then, a deterministic approach is used to calculate the point estimates of parameters for the selected method. This approach, however, may not account for uncertainty associated with reservoir production behavior.

Over time, changes in field operating conditions take place to maintain the desired production target output. These may include changes in well operating settings, workover or change in artificial lift, etc. Subsequently, these changes re reflected in the well production behavior. Engineers need to pick the correct event so that the actual well behavior is represented. Many times, the fit used to determine DCA parameters is obtained on the entire history even though the data do not seem to follow the assumptions laid earlier.

SUMMARY

Embodiments of the disclosure provide a method that includes receiving historical well-production data, and determining curve parameters based on the historical well production data. Determining the curve parameters includes accounting for uncertainty. The method also includes determining curve fits for the historical data based on the curve parameters using a plurality of models, calculating accuracy for each of the models based on a comparison of the curve fits to the well-production data, comparing the accuracy for each of the models using an information criteria that accounts for uncertainty, selecting one of the models based on the comparison, and determining an estimated ultimate recovery (EUR) for the well using at least the selected one of the models.

Embodiments of the disclosure provide a non-transitory computer-readable medium storing instructions that, when executed by at least one processor of a computing system, cause the computing system to perform operations. The operations include receiving historical well-production data, and determining curve parameters based on the historical well production data. Determining the curve parameters includes accounting for uncertainty. The operations also include determining curve fits for the historical data based on the curve parameters using a plurality of models, calculating accuracy for each of the models based on a comparison of the curve fits to the well-production data, comparing the accuracy for each of the models using an information criteria that accounts for uncertainty, selecting one of the models based on the comparison, and determining an estimated ultimate recovery (EUR) for the well using at least the selected one of the models.

Embodiments of the disclosure provide a computing system that includes one or more processors, and a memory system including one or more non-transitory computer-readable media storing instructions that, when executed by at least one of the one or more processors, cause the computing system to perform operations. The operations include receiving historical well-production data, and determining curve parameters based on the historical well production data. Determining the curve parameters includes accounting for uncertainty. The operations also include determining curve fits for the historical data based on the curve parameters using a plurality of models, calculating accuracy for each of the models based on a comparison of the curve fits to the well-production data, comparing the accuracy for each of the models using an information criteria that accounts for uncertainty, selecting one of the models based on the comparison, and determining an estimated ultimate recovery (EUR) for the well using at least the selected one of the models.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The accompanying drawings, which are incorporated in and constitute a part of this specification, illustrate embodiments of the present teachings and together with the description, serve to explain the principles of the present teachings. In the figures.

DETAILED DESCRIPTION

Reference will now be made in detail to embodiments, examples of which are illustrated in the accompanying drawings and figures. In the following detailed description, numerous specific details are set forth in order to provide a thorough understanding of the invention. However, it will be apparent to one of ordinary skill in the art that the invention may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the present disclosure. The first object or step, and the second object or step, are both, objects or steps, respectively, but they are not to be considered the same object or step.

The terminology used in the description herein is for the purpose of describing particular embodiments and is not intended to be limiting. As used in this description and the appended claims, the singular folios "a," "an" and "the" are intended to include the plural forms as well, unless the context clearly indicates otherwise. It will also be understood that the term "and/or" as used herein refers to and encompasses any possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Further, as used herein, the term "if" may be construed to mean "when" or "upon" or "in response to determining" or "in response to detecting," depending on the context.

Attention is now directed to processing procedures, methods, techniques, and workflows that are in accordance with some embodiments. Some operations in the processing procedures, methods, techniques, and workflows disclosed herein may be combined and/or the order of some operations may be changed.

Figure 1:
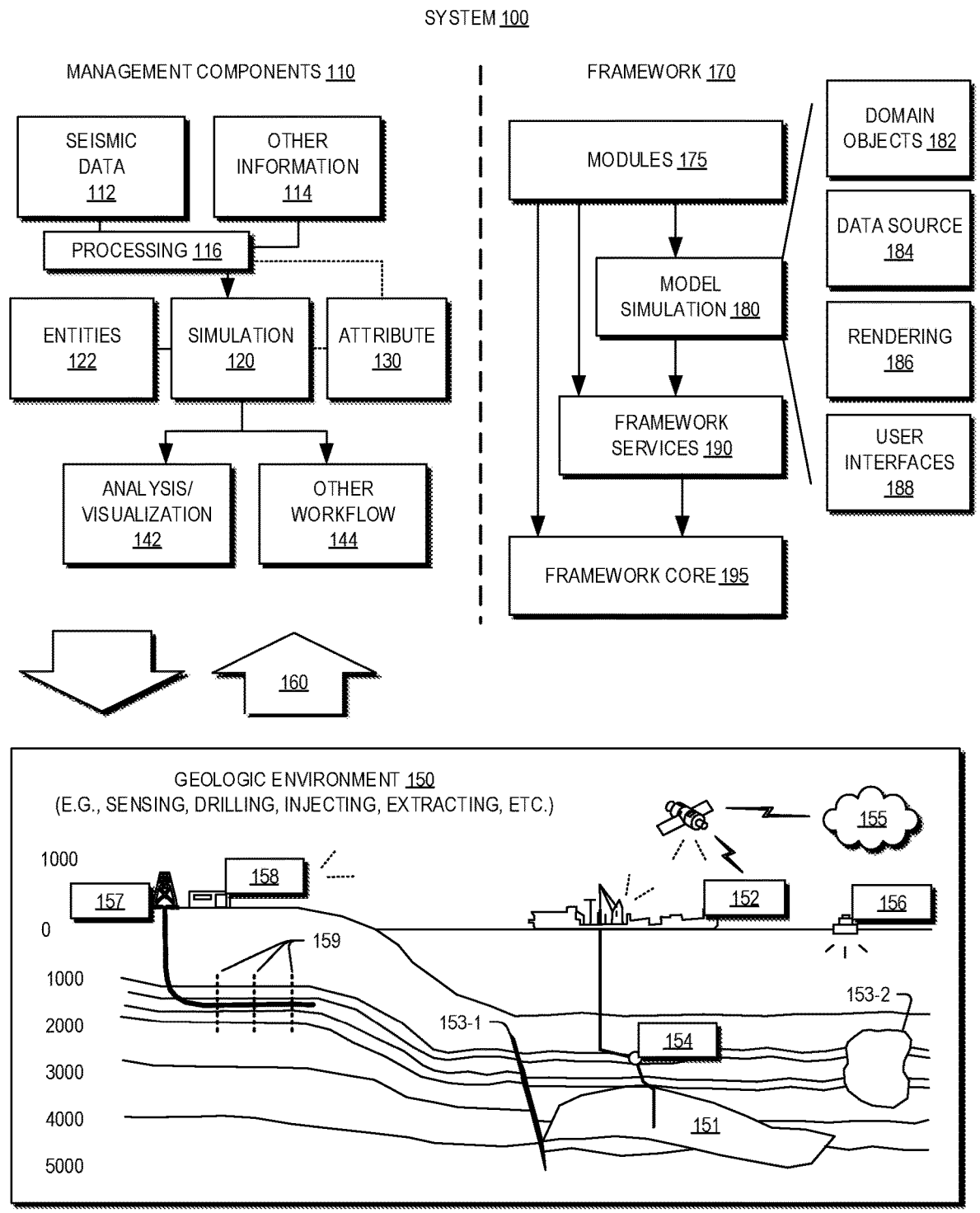
FIG. 1 illustrates an example of a system that includes various management components to manage various aspects of a geologic environment, according to an embodiment.

FIG. 1 illustrates an example of a system 100 that includes various management components 110 to manage various aspects of a geologic environment 150 (e.g., an environment that includes a sedimentary basin, a reservoir 151, one or more faults 153-1, one or more geobodies 153-2, etc.). For example, the management components 110 may allow for direct or indirect management of sensing, drilling, injecting, extracting, etc., with respect to the geologic environment 150. In turn, further information about the geologic environment 150 may become available as feedback 160 (e.g., optionally as input to one or more of the management components 110).

In the example of FIG. 1, the management components 110 include a seismic data component 112, an additional information component 114 (e.g., well/logging data), a processing component 116, a simulation component 120, an attribute component 130, an analysis/visualization component 142 and a workflow component 144. In operation, seismic data and other information provided per the components 112 and 114 may be input to the simulation component 120.

In an example embodiment, the simulation component 120 may rely on entities 122. Entities 122 may include earth entities or geological objects such as wells, surfaces, bodies, reservoirs, etc. In the system 100, the entities 122 can include virtual representations of actual physical entities that are reconstructed for purposes of simulation. The entities 122 may include entities based on data acquired via sensing, observation, etc. (e.g., the seismic data 112 and other information 114). An entity may be characterized by one or more properties (e.g., a geometrical pillar grid entity of an earth model may be characterized by a porosity property). Such properties may represent one or more measurements (e.g., acquired data), calculations, etc.

In an example embodiment, the simulation component 120 may operate in conjunction with a software framework such as an object-based framework. In such a framework, entities may include entities based on pre-defined classes to facilitate modeling and simulation. A commercially available example of an object-based framework is the MICROSOFT® .NET® framework (Redmond, Wash.), which provides a set of extensible object classes. In the .NET® framework, an object class encapsulates a module of reusable code and associated data structures. Object classes can be used to instantiate object instances for use in by a program, script, etc. For example, borehole classes may define objects for representing boreholes based on well data.

In the example of FIG. 1, the simulation component 120 may process information to conform to one or more attributes specified by the attribute component 130, which may include a library of attributes. Such processing may occur prior to input to the simulation component 120 (e.g., consider the processing component 116). As an example, the simulation component 120 may perform operations on input information based on one or more attributes specified by the attribute component 130. In an example embodiment, the simulation component 120 may construct one or more models of the geologic environment 150, which may be relied on to simulate behavior of the geologic environment 150 (e.g., responsive to one or more acts, whether natural or artificial). In the example of FIG. 1, the analysis/visualization component 142 may allow for interaction with a model or model-based results (e.g., simulation results, etc.). As an example, output from the simulation component 120 may be input to one or more other workflows, as indicated by a workflow component 144.

As an example, the simulation component 120 may include one or more features of a simulator such as the ECLIPSE™ reservoir simulator (Schlumberger Limited, Houston Tex.), the INTERSECT™ reservoir simulator (Schlumberger Limited, Houston Tex.), etc. As an example, a simulation component, a simulator, etc. may include features to implement one or more meshless techniques (e.g., to solve one or more equations, etc.). As an example, a reservoir or reservoirs may be simulated with respect to one or more enhanced recovery techniques (e.g., consider a thermal process such as SAGD, etc.).

In an example embodiment, the management components 110 may include features of a commercially available framework such as the PETREL® seismic to simulation software framework (Schlumberger Limited, Houston, Tex.). The PETREL® framework provides components that allow for optimization of exploration and development operations. The PETREL® framework includes seismic to simulation software components that can output information for use in increasing reservoir performance, for example, by improving asset team productivity. Through use of such a framework, various professionals (e.g., geophysicists, geologists, and reservoir engineers) can develop collaborative workflows and integrate operations to streamline processes. Such a framework may be considered an application and may be considered a data-driven application (e.g., where data is input for purposes of modeling, simulating, etc.).

In an example embodiment, various aspects of the management components 110 may include add-ons or plug-ins that operate according to specifications of a framework environment. For example, a commercially available framework environment marketed as the OCEAN® framework environment (Schlumberger Limited, Houston, Tex.) allows for integration of add-ons (or plug-ins) into a PETREL® framework workflow. The OCEAN® framework environment leverages .NET® tools (Microsoft Corporation, Redmond, Wash.) and offers stable, user-friendly interfaces for efficient development. In an example embodiment, various components may be implemented as add-ons (or plug-ins) that conform to and operate according to specifications of a framework environment (e.g., according to application programming interface (API) specifications, etc.).

FIG. 1 also shows an example of a framework 170 that includes a model simulation layer 180 along with a framework services layer 190, a framework core layer 195 and a modules layer 175. The framework 170 may include the commercially available OCEAN® framework where the model simulation layer 180 is the commercially available PETREL® model-centric software package that hosts OCEAN® framework applications. In an example embodiment, the PETREL® software may be considered a data-driven application. The PETREL® software can include a framework for model building and visualization.

As an example, a framework may include features for implementing one or more mesh generation techniques. For example, a framework may include an input component for receipt of information from interpretation of seismic data, one or more attributes based at least in part on seismic data, log data, image data, etc. Such a framework may include a mesh generation component that processes input information, optionally in conjunction with other information, to generate a mesh.

In the example of FIG. 1, the model simulation layer 180 may provide domain objects 182, act as a data source 184, provide for rendering 186 and provide for various user interfaces 188. Rendering 186 may provide a graphical environment in which applications can display their data while the user interfaces 188 may provide a common look and feel for application user interface components.

As an example, the domain objects 182 can include entity objects, property objects and optionally other objects. Entity objects may be used to geometrically represent wells, surfaces, bodies, reservoirs, etc., while property objects may be used to provide property values as well as data versions and display parameters. For example, an entity object may represent a well where a property object provides log information as well as version information and display information (e.g., to display the well as part of a model).

In the example of FIG. 1, data may be stored in one or more data sources (or data stores, generally physical data storage devices), which may be at the same or different physical sites and accessible via one or more networks. The model simulation layer 180 may be configured to model projects. As such, a particular project may be stored where stored project information may include inputs, models, results and cases. Thus, upon completion of a modeling session, a user may store a project. At a later time, the project can be accessed and restored using the model simulation layer 180, which can recreate instances of the relevant domain objects.

In the example of FIG. 1, the geologic environment 150 may include layers (e.g., stratification) that include a reservoir 151 and one or more other features such as the fault 153-1, the geobody 153-2, etc. As an example, the geologic environment 150 may be outfitted with any of a variety of sensors, detectors, actuators, etc. For example, equipment 152 may include communication circuitry to receive and to transmit information with respect to one or more networks 155. Such information may include information associated with downhole equipment 154, which may be equipment to acquire information, to assist with resource recovery, etc. Other equipment 156 may be located remote from a well site and include sensing, detecting, emitting or other circuitry. Such equipment may include storage and communication circuitry to store and to communicate data, instructions, etc. As an example, one or more satellites may be provided for purposes of communications, data acquisition, etc. For example, FIG. 1 shows a satellite in communication with the network 155 that may be configured for communications, noting that the satellite may additionally or instead include circuitry for imagery (e.g., spatial, spectral, temporal, radiometric, etc.).

FIG. 1 also shows the geologic environment 150 as optionally including equipment 157 and 158 associated with a well that includes a substantially horizontal portion that may intersect with one or more fractures 159. For example, consider a well in a shale formation that may include natural fractures, artificial fractures (e.g., hydraulic fractures) or a combination of natural and artificial fractures. As an example, a well may be drilled for a reservoir that is laterally extensive. In such an example, lateral variations in properties, stresses, etc. may exist where an assessment of such variations may assist with planning, operations, etc. to develop a laterally extensive reservoir (e.g., via fracturing, injecting, extracting, etc.). As an example, the equipment 157 and/or 158 may include components, a system, systems, etc. for fracturing, seismic sensing, analysis of seismic data, assessment of one or more fractures, etc.

As mentioned, the system 100 may be used to perform one or more workflows. A workflow may be a process that includes a number of worksteps. A workstep may operate on data, for example, to create new data, to update existing data, etc. As an example, a may operate on one or more inputs and create one or more results, for example, based on one or more algorithms. As an example, a system may include a workflow editor for creation, editing, executing, etc. of a workflow. In such an example, the workflow editor may provide for selection of one or more pre-defined worksteps, one or more customized worksteps, etc. As an example, a workflow may be a workflow implementable in the PETREL® software, for example, that operates on seismic data, seismic attribute(s), etc. As an example, a workflow may be a process implementable in the OCEAN® framework. As an example, a workflow may include one or more worksteps that access a module such as a plug-in (e.g., external executable code, etc.).

Embodiments of the system and method disclosed herein integrate exposed analogue models (e.g., into PETREL®) with other types of input data (e.g., seismic and well logs), while adding confidence and reducing uncertainty. As described in greater detail below, the system and method include automated and quantitative analysis of exposed analogues; automated geostatistical analysis of the reservoir properties; sedimentary forward modelling; synthetic seismic generation and matching to subsurface seismic data; and training data generation for subsurface interpretation constrained by geological rules derived from analogues. The resulting reservoir model is then the input for fluid flow simulation technologies. The optimal integration of multi-type datasets may improve the knowledge transfer from ground to subsurface, increasing the efficiency and consistency in modeling complex reservoirs to ultimately reduce exploration risks and improve reservoir management.

Embodiments of the present disclosure may provide a probabilistic forecasting method and a system that implements such methods that builds stochastic models for production data including, among others, outliers, pressure changes, different flow regimes, and downtime. The method provides an ensemble approach including change-point detection, density-based segregation, and Bayesian inferences, embedded within an automated statistical framework. As part of the method, a model is employed that picks workover interventions that occurred on the wells and uses these picks to divide the historical data into different segments, then removes outliers from history, models decline behavior, determines best forecasting method for each well, and estimates future production and associated uncertainty. In some embodiments, the method leverages prior knowledge of the field and well characteristics, incorporates continuous learning, and performs automated model selection to determine the best forecast for a well under study.

Using the process, a production engineer can determine the conditional dependence among different drivers of well performance, forecasting techniques, well events, and operating conditions for the wells under analysis. Localized models obtained through different segments of production data with periods of natural decline help in understanding well behavior better and modeling the trend leading to a workover.

This information can be used to predict the benefit of a workover. The proposed application workflow also reduces the turnaround time of performing production forecast for an asset being analyzed from weeks and months to hours and improves the quality of reserves. Wells with highly accurate forecasts may be automatically published in the application, and which may eliminate the manual selection for such wells.

1. Statistical Engine a. Event Segmentation

Figure 2:
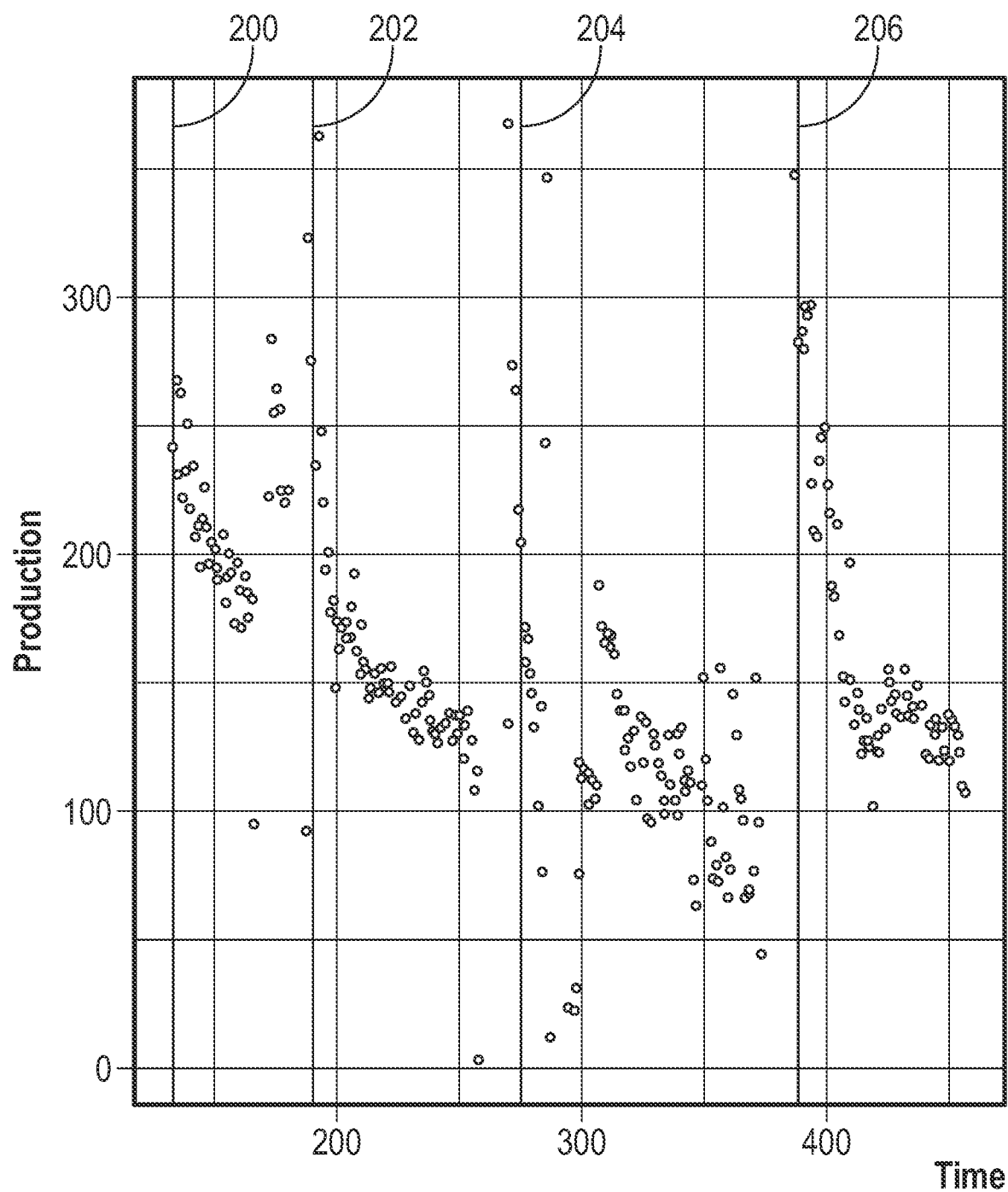
FIG. 2 illustrates a plot of well production data versus time, according to an embodiment.

FIG. 2 illustrates a plot of well production data versus time, according to an embodiment, showing segmentation lines 200, 202, 204, 206, representing events identified in the data which result in changes in behavior of the well. Identifying trends in well production behavior facilitates making accurate forecast predictions. A change in flow regime or well production strategy may result in a new decline behavior for a well. Over the life of the well, the well may experience many such events leading to changes in production behavior. These "behavior-changing" events can be well interventions or workovers, among other possibilities. Further, these events may be captured and related to changes in patterns in well behavior so that the future production is correctly estimated. In some situations, there may be no records about the time and type of such events in the past. Even if some logs exist, the data may be fragmented or inaccessible. This may result in production analysis per well being a manual process.

An unsupervised modeling workflow to detect workovers or well interventions using the history may use the principles of Discrete Wavelet Transform (DWT) coupled with denoising, thresholding, and post processing using a priori information. In DWT operations, wavelet decomposition may be performed on the time series production data by using a non-downsampled version of DWT, applying wavelet filters, and performing multilevel decomposition to extract discriminant features at various levels.

The DWT decomposes by decimating in powers of, e.g., two, and filtering. These two different operations, taken together, may decompose the signal into low-frequency and high-frequency sub-bands. The low-pass filter extracts the approximate information of the signal, and the high-pass filter extracts the details such as edges. The wavelet coefficients obtained at the various levels of decomposition may be analyzed, and an additional operation of denoising may be performed. A threshold may be applied to the signal, based on a statistical threshold criterion. Samples below the threshold may be removed in a sub-band, and samples above the threshold may be retained. After thresholding, the peaks across each of the wavelet coefficients may be determined, and the combined picks may then be passed through a moving window to further produce one pick in a defined time window. Using this approach, production behavior-changing events, such as workovers or operational interventions may be identified.

b. Outlier Identification and Removal

Figure 3:
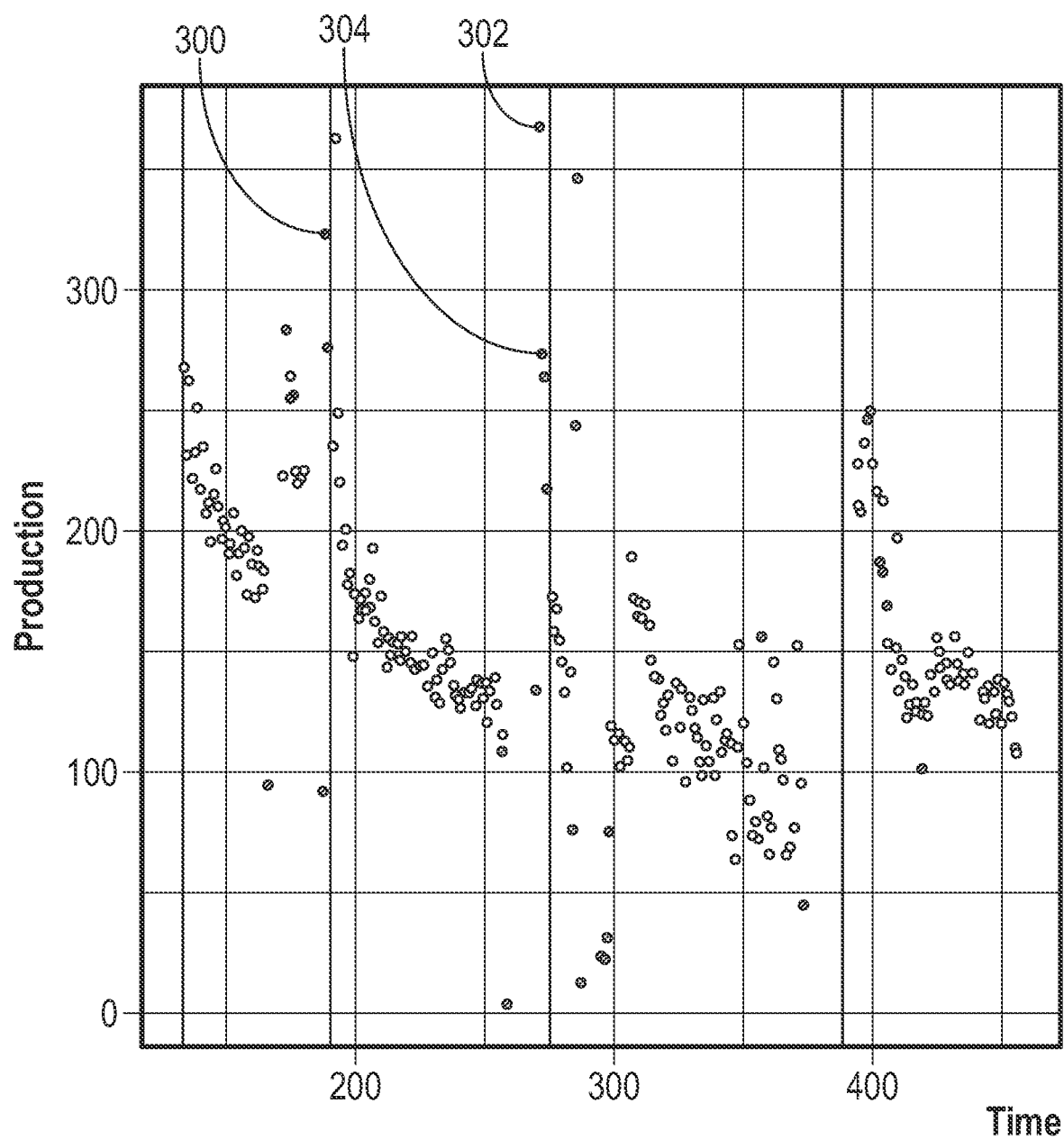
FIG. 3 illustrates a plot of well production versus time in which outliers have been identified, according to an embodiment.

FIG. 3 illustrates a plot of well production versus time in which outliers (e.g., points 300, 302, 304) have been identified, according to an embodiment. Outliers represent the data points that are distant from other observations and may not represent the actual well production behavior. The outliers may be a result of incorrect measurements, manual errors, or well operational issues. Outliers can cause bias in the analysis and may be removed so that the data used for curve fitting accurately represents production behavior trends in a well. Generally, a production engineer may manually inspect the data and identifies outliers when well historical event records are available. Employing an automatic statistical approach, on the other hand, to determine the outliers may remove bias from manual interpretation and enable a consistent approach in data preprocessing.

In some embodiments, a density-based, spatial clustering algorithm may be used to identify outliers across each production segment obtained after event segmentation. Given a set of data points in the space, this methodology groups points that are close to one another given a predefined metric and minimum number of points per cluster. Points belonging to low-density regions were identified and marked as the outliers 300, 302, 304 and may be ignored, discounted, or otherwise given less weight during subsequent analysis.

c. Probabilistic Model for Curve Fit and Forecasts

Figure 4:
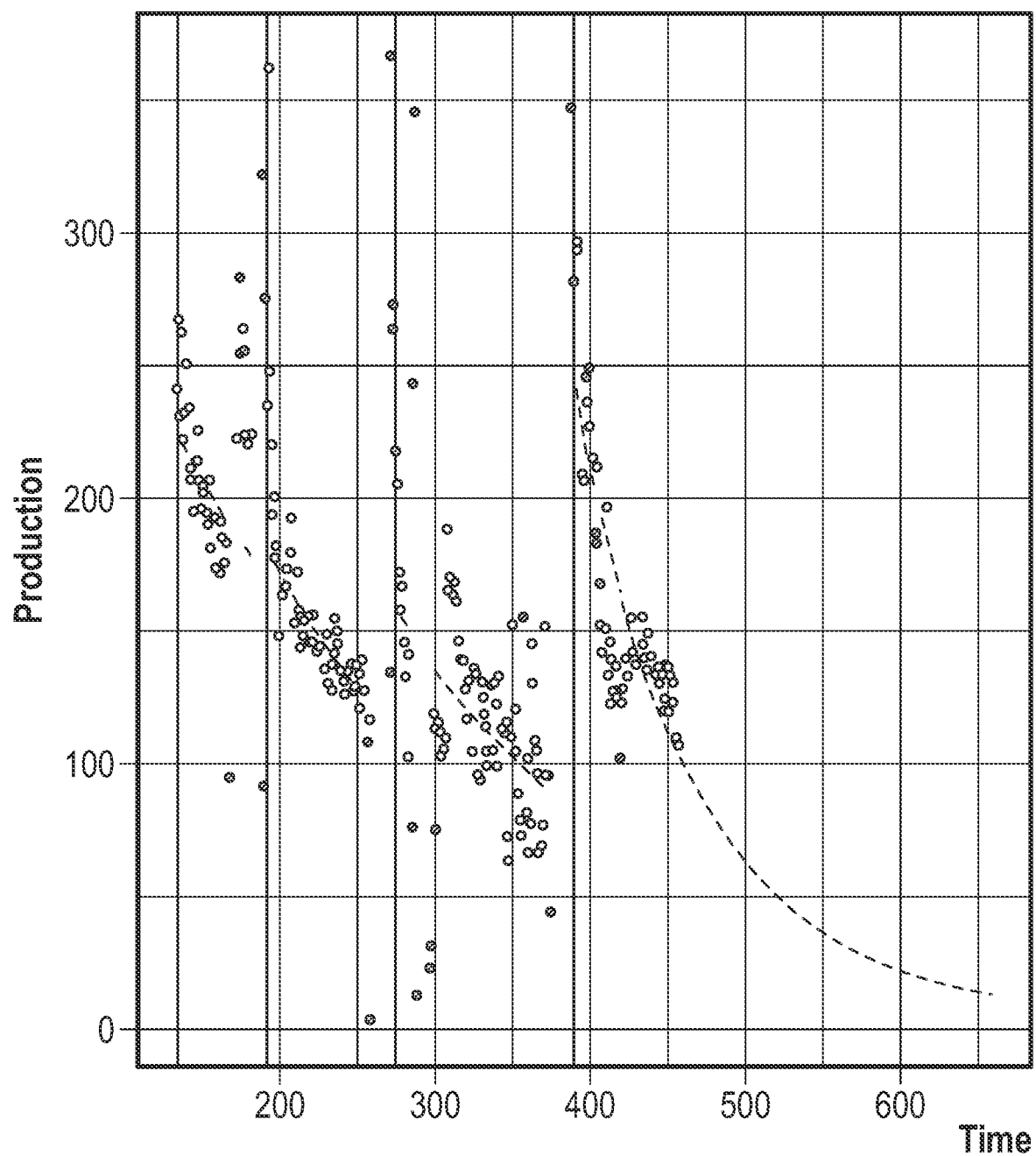
FIG. 4 illustrates a curve fit and prediction result for a well using an embodiment of the present disclosure.

FIG. 4 illustrates a curve fit and prediction result for a well using an embodiment of the present disclosure. After periods with natural decline are identified and outliers are removed, as described above, the parameters of different forecasting techniques may be determined using Bayesian inference. The Bayesian model allows incorporation of previous knowledge or beliefs into the model and allows derivation of probabilistic inferences for the outcome of interest. In frequentist inference, parameters are estimated as fixed quantities, whereas in Bayesian inference, parameters are considered as random quantities following certain distributions. Bayesian inference helps in modeling a complex system with many unknown parameters.

Bayesian inference also considers the prior uncertainties of model parameters and updates the prior beliefs with the data to form posterior distribution. In this methodology, beliefs or information related to observed field characteristics are incorporated as priors into the Bayesian model. In the absence of supporting data, evidence based on historical data or assessment of the field by domain experts can be used as the priors. Bayesian analysis may call for defining a likelihood function tailored to each decline curve such as advanced regional prediction systems (ARDS), Duong, etc.

The prior and likelihood are joined in accordance with Bayes' law to produce the posterior distribution, followed by a two-part approach. In the first part, the approach includes determining maximum a posteriori estimates representing the mode of the posterior distribution. To determine the model, Broyden-Fletcher-Goldfarb-Shanno (BFGS) algorithm, a quasi-Newton method that employs exactly computed gradients and an efficient approximation to the Hessian may be used. The model converges when the value of the objective function (e.g., log probability) reaches the specified tolerance. In the second part, the approach includes characterizing the distribution of the parameters to approximate a closed form solution using a sampling scheme. In this manner, parameters may be estimated for each of the forecasting techniques (models) that fit the curve segments.

Production trends in the near future can be influenced by the last workover performed on the well, because a workover may influence the decline characteristics of the well. Therefore, by being able to segment the well history into periods of natural decline using the events segmentation model, parameters obtained for the last segment may be used to estimate production into the future. Fit through the previous segments may be employed to infer the characteristics of well interventions that have been conducted on a particular well, so as to assist in predicting the impact of subsequent workovers of the same type.

d. Uncertainty Estimation

Figure 5:
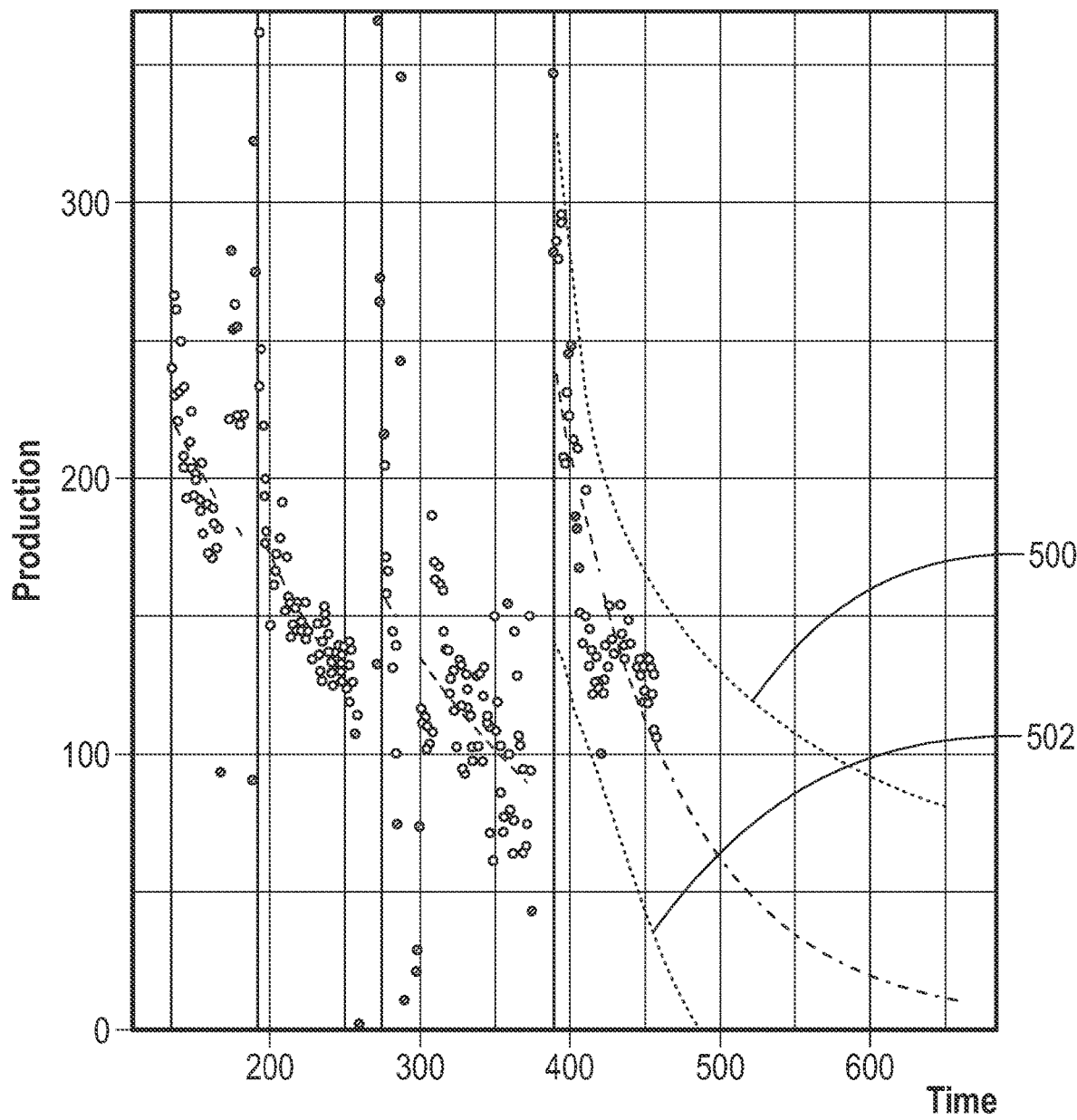
FIG. 5 illustrates a plot of production with uncertainty bands across the last segment (e.g., after the last-in-time behavior-changing event) and the prediction, according to an embodiment.

FIG. 5 illustrates a plot of production with uncertainty bands 500, 502 across the last segment and the prediction. Bayesian inferences uses probability to quantify the uncertainty. Using the observed data and the calculated posteriors across several (many) timesteps, the uncertainty bands may be determined. The uncertainty bands may represent the, e.g., 90%, prediction interval for the data. The uncertainty bands may be checked to determine if they bound the actual, observed data and to determine if there were any systematic deviations of the observed data from the model.

e. Model Accuracy

Posterior predictive checks may be employed to validate the model created using the methodology discussed above. The degree to which the data simulated from the model deviate from the observed data may be analyzed. The deviation may indicate if the posterior distribution is approximating the underlying distribution. This accuracy determination may be repeated for each forecasting technique.

f. Model Comparison

The results obtained from different parametric models may be compared using Bayesian Information Criteria (BIC). BIC helps measure the quality of the models. This criterion is defined as $BIC=k\log n - 2*LL$, where $LL$ is the log-likelihood of the model, $k$ is the number of estimated parameters, and $n$ is the number of data points. BIC measures the efficiency of the parameterized model in terms of predictive power. The model with lowest BIC value may be selected as the most accurate model.

2. Application to Interpret and Manage Well Operations

Figure 6:
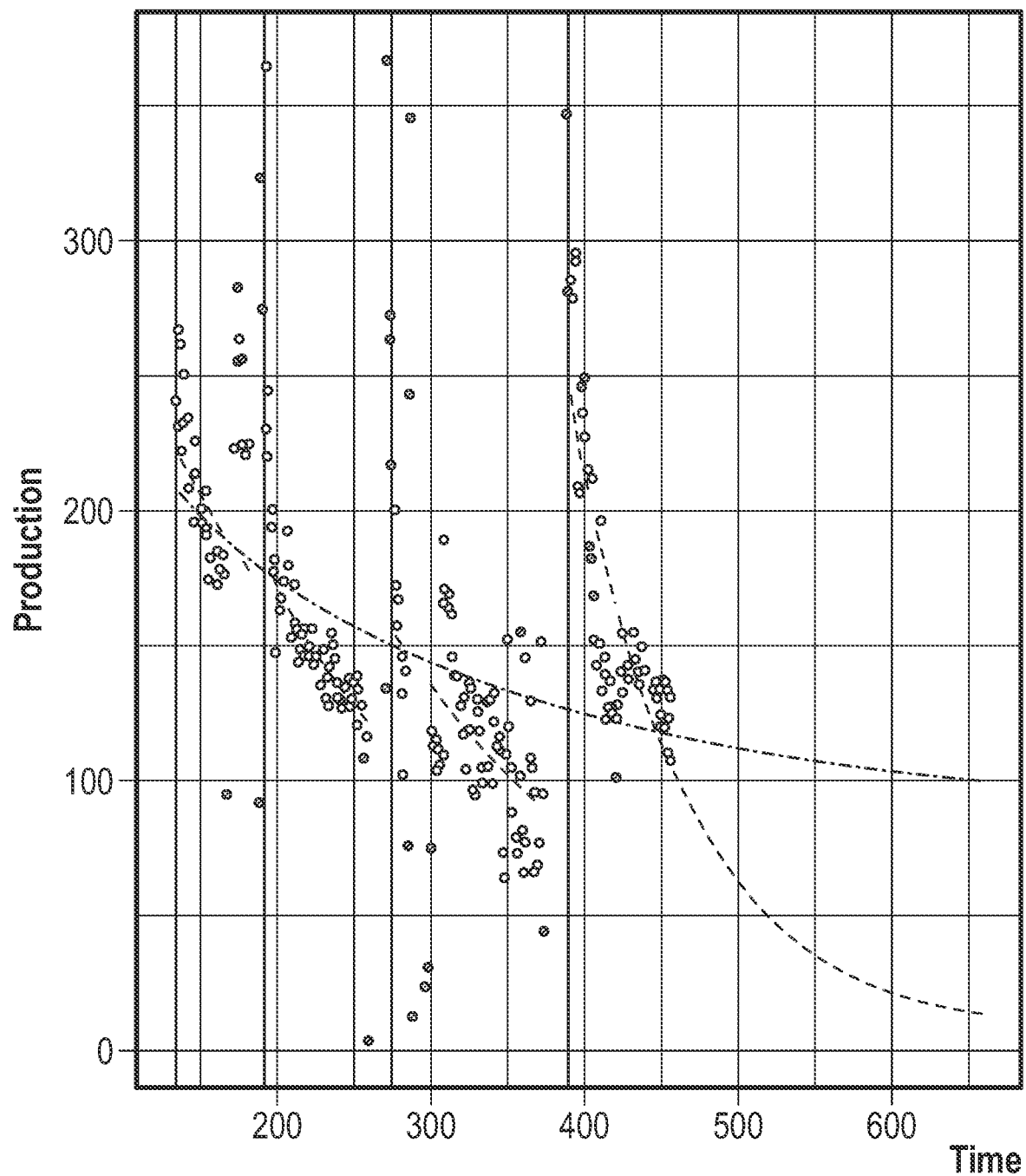
FIG. 6 illustrates a plot of the curve fit and forecasts without segmentation.
Figure 7:
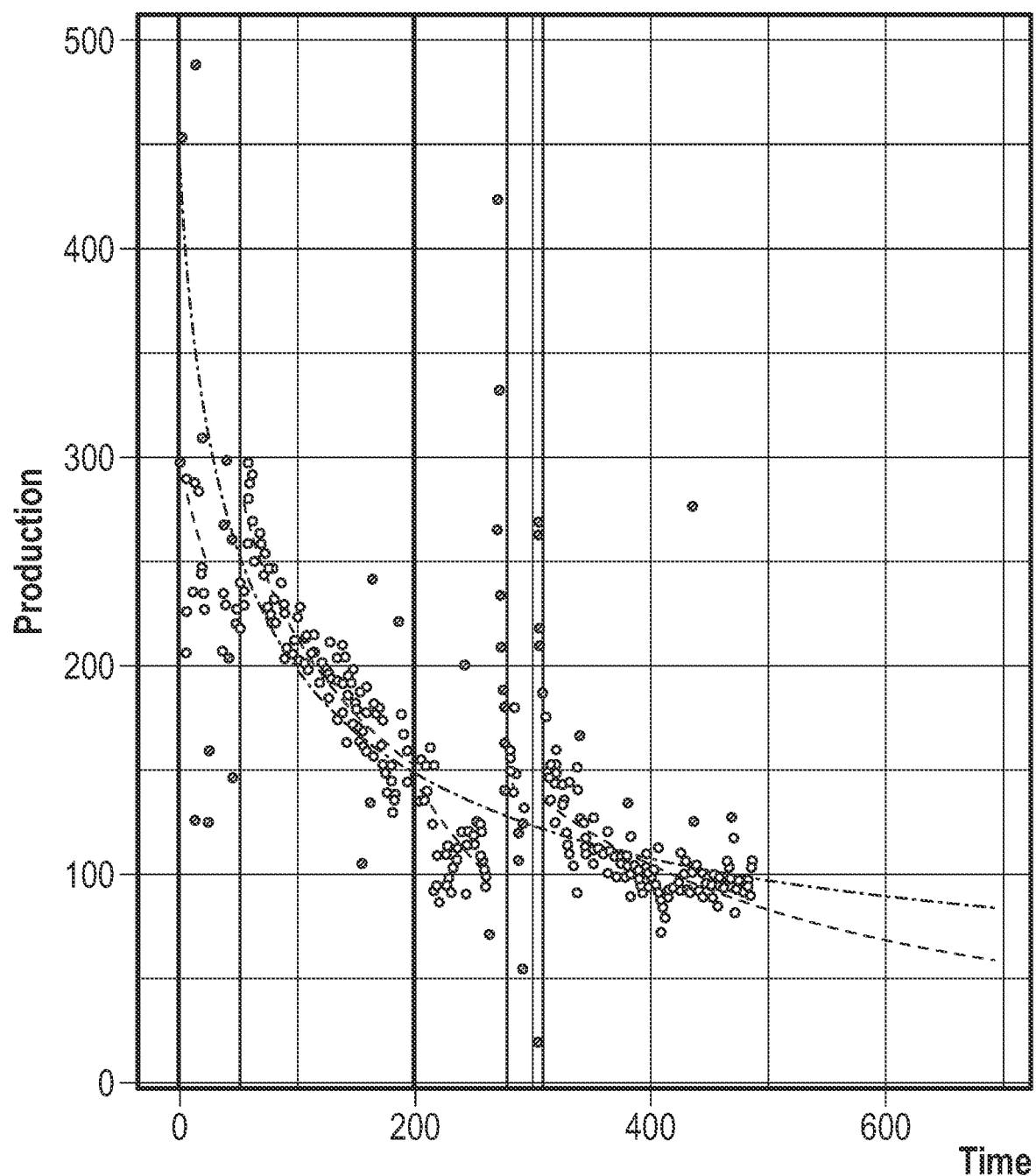
FIG. 7 illustrates a plot of the curve fit and forecasts with segmentation.

Embodiments of the present disclosure may be employed in well operations planning and management. FIG. 6 illustrates a plot of the curve fit and forecasts without segmentation, and FIG. 7 illustrates a plot of the curve fit and forecasts with segmentation. The production predictions for both the sample wells are different in the two cases. Thus, identifying workovers and modeling their influence on production behavior can help avoid overestimating or underestimating future production and reserves. Furthermore, when comparing the two wells, the jump in production due to the last workover may not be significant in some cases, while in other cases, e.g., in the illustrated production log, it is. Forecasts may be based on the natural decline after the last-in-time behavior-changing event, e.g., unless/until a forecasted next behavior-changing event may occur.

The scope of this model can be further extended. By modeling the change in production signature due to workovers, classes of workovers can be identified and such classes can be ranked based on their ability to maximize production and recoverable reserves. This ranking scheme can be used while planning workover activity on underperforming wells. Further, the fit through each of the production segments obtained from the event segmentation model can be extended to predict the production decline as if no further workover was performed on that well. The estimated production in this case is then compared against the actual total production due to the workover that succeeded the segment. The value of production increase is then analyzed against the costs incurred in performing that workover to determine if the intervention is an effective activity or not. In this manner, the model can serve as a recommendation system to propose specific, most-effective workover with the lowest costs and highest rate of return that should be performed on well given a well's production data.

Accordingly, embodiments of the present disclosure may model the stochastic nature of production data and well behavior for both conventional and unconventional assets. In the absence of labels or records of workovers, the workflow automatically detects behavior-changing events thorough an unsupervised modeling approach, which considers the declining production pattern. It further leverages prior knowledge, incorporates feedback from production engineers, determines production uncertainty and performs automated model selection to select a forecasting model given well data. In this manner, the statistical engine helps predict production potential and estimated ultimate recovery (EUR). In some conventional processes, it takes a production engineer or asset manager approximately a day to manually select outliers, perform forecasts, analyze different forecasting techniques, and determine EUR for 15 to 20 wells. Moreover, predictions from this traditional workflow are highly uncertain as typically events are ignored and uncertainty is not estimated. When repeated on all the wells in the field, this process is costly in work-hours to investigate a field having of hundreds of wells. The proposed workflow provides a system to study well interventions, automates forecasting, and helps improve the effectiveness and efficiency of people and operations.

Figure 8:
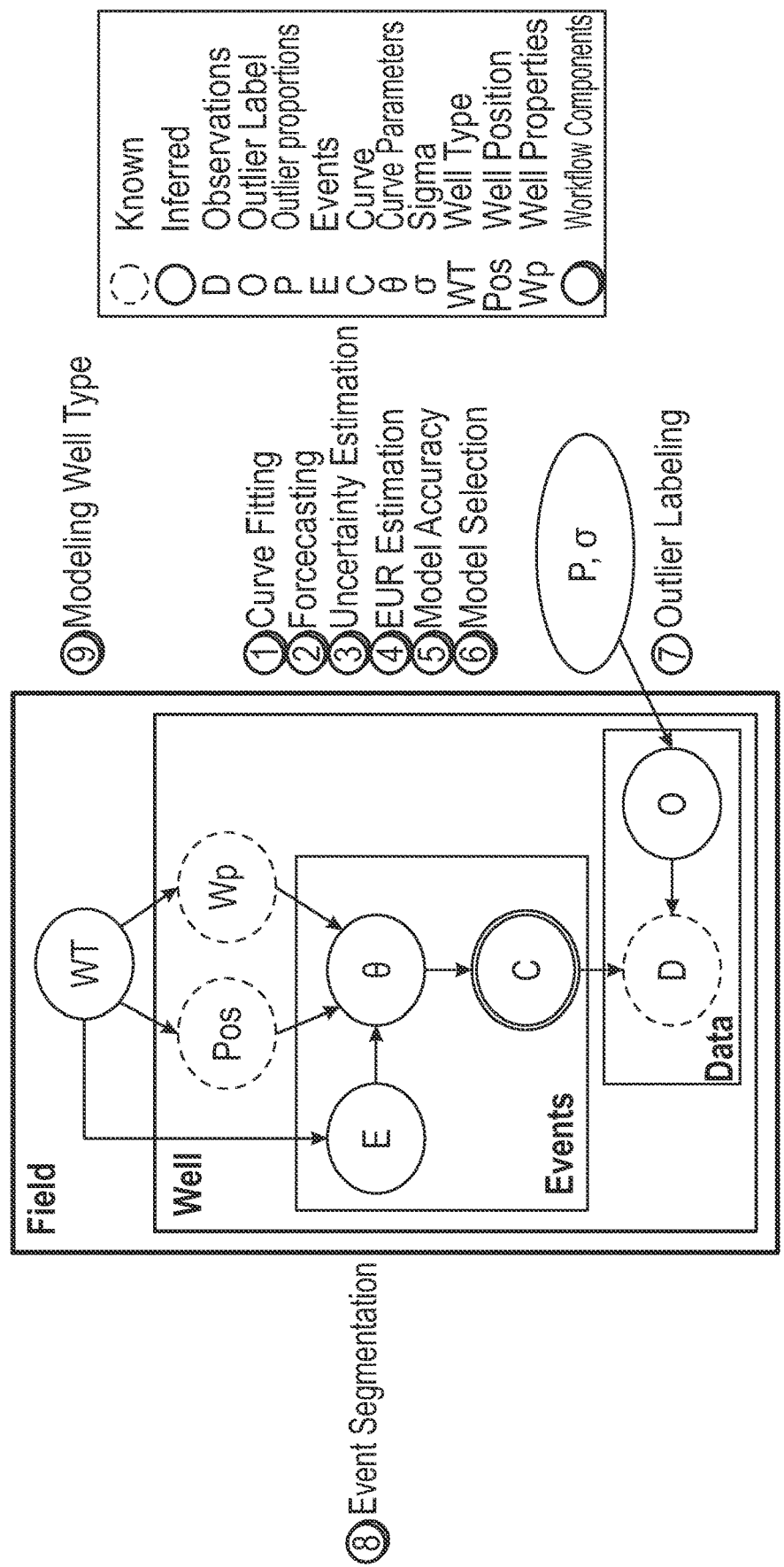
FIG. 8 illustrates a graphical asset network model, according to an embodiment.

3. Workflow for Using a Probabilistic Framework to Automate Production Forecasting The analytical engine is a probabilistic model which expresses the conditional dependence between different drivers of well performance, forecasting techniques, events and operating conditions. FIG. 8 illustrates a graphical asset network model, according to an embodiment. The model represents a graph-based representation of the Bayesian network structure and depicts the factorized representation of the random variables used to build the features of the application workflow for the asset including plate models for the field, the wells in the field, the event in the well, and production data for each event per well.

As shown, a field represents the basic level, and the variables associated therewith include well types WT present in the field. The well types may be inferred. Accordingly, each field has wells associated therewith. The wells include variables of well position Pos and well properties Wp, which may be a prior known. Within each well 500, there may be events and data 504. In the events, variables may include event E, curve parameters θ and curve C. Events E maybe inferred from well type, and curve parameters may be inferred from events E, position, and well properties Wp, and from these parameters the curve C, which may be extrapolated to forecast future production may be determined. Within the data, the variables may be observations D, which may be known, and outlier labels O, which may be calculated as noted above. Outlier proportion P and noise σ may be calculated and used to determine the outlier labels O.

Figure 9:
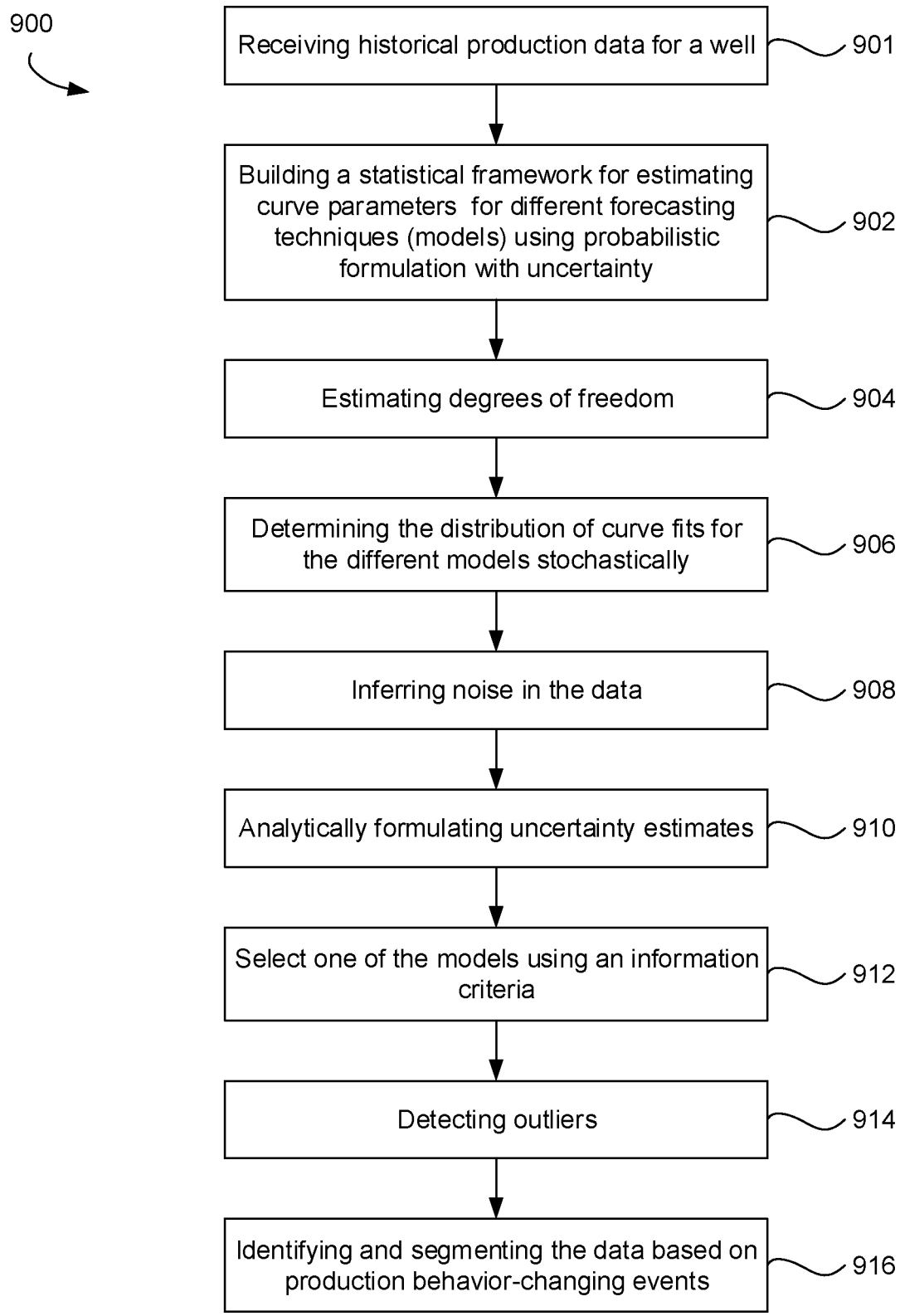
FIG. 9 illustrates a flowchart for a probabilistic forecasting method, according to an embodiment.

The modeling method leading up to the graphical model for the complete asset as shown in involves a modeling method. FIG. 9 illustrates a flowchart for a probabilistic forecasting method 900 (i.e., a modeling method), according to an embodiment. The method 900 includes receiving historical production data for a well, as at 901. The production data may provide data points for production versus time.

The method 900 includes building a statistical framework for estimating curve parameters (see, e.g., section 1.c above) for different forecasting techniques (models) given historical production data using probabilistic formulation with uncertainty, extensible to any curve, as at 902. The method 900 may also include estimating degrees of freedom by performing experiments to compare shape of data distributions for production data across conventional and unconventional wells against t distribution with different degrees of freedom, as at 904. The degrees of freedom may be internal to the model and thus are not shown in FIG. 8.

The method 900 may also include determining the distribution of curve fits for the different models, including best fit, fit with least standard error, variance, etc., stochastically using Markov Chain Monte Carlo (MCMC) data sampling, as at 906. This may include modeling the entire distribution using maximum posterior estimates, e.g., as described above in section 1.c. The method 900 may also include inferring noise σ in the data, as at 908. The method 900 may then proceed to analytically formulating uncertainty (e.g., P10-P90) estimates by factoring in the noise in the data, as at 910.

Figure 10:
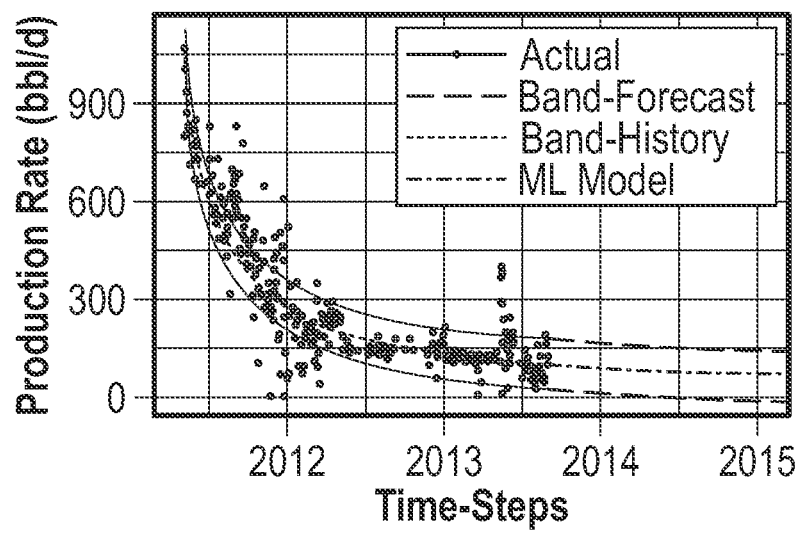
FIG. 10 illustrates a plot of production versus time which includes curve fitting to production data containing outliers, forecast generation and associated uncertainty quantification, according to an embodiment.
Figure 11:
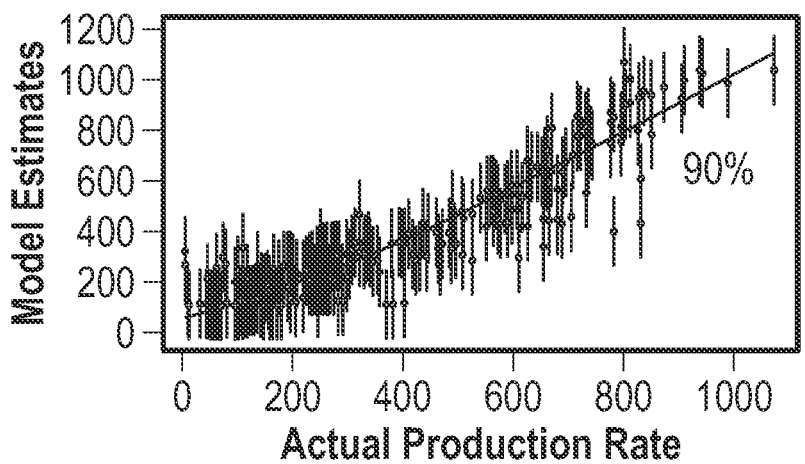
FIG. 11 illustrates calculating model accuracy using predictive concordance for estimates within 80% probability interval, according to an embodiment.
Figure 12:
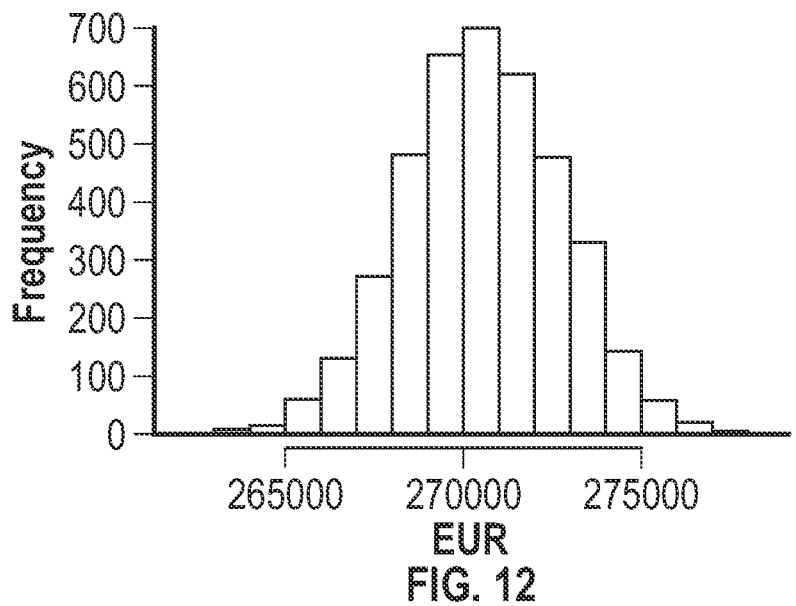
FIG. 12 illustrates a histogram of estimated ultimate recovery (EUR) values for different wells using an example model.

By way of illustrating the foregoing aspects of the method 900, FIG. 10 illustrates a plot of production versus time which includes curve fitting to production data containing outliers, forecast generation and associated uncertainty quantification, according to an embodiment. Further, FIG. 11 illustrates calculating model accuracy using predictive concordance for estimates within 80% probability interval. In this plot, for each timestep, the range of the estimates obtained from the model and the mean value of those estimates is indicated. FIG. 12 illustrates a histogram of EUR values for different wells using an example model. In particular, estimating EUR using best fit parameter estimates and the EUR distribution using posterior samples.

Figure 13:
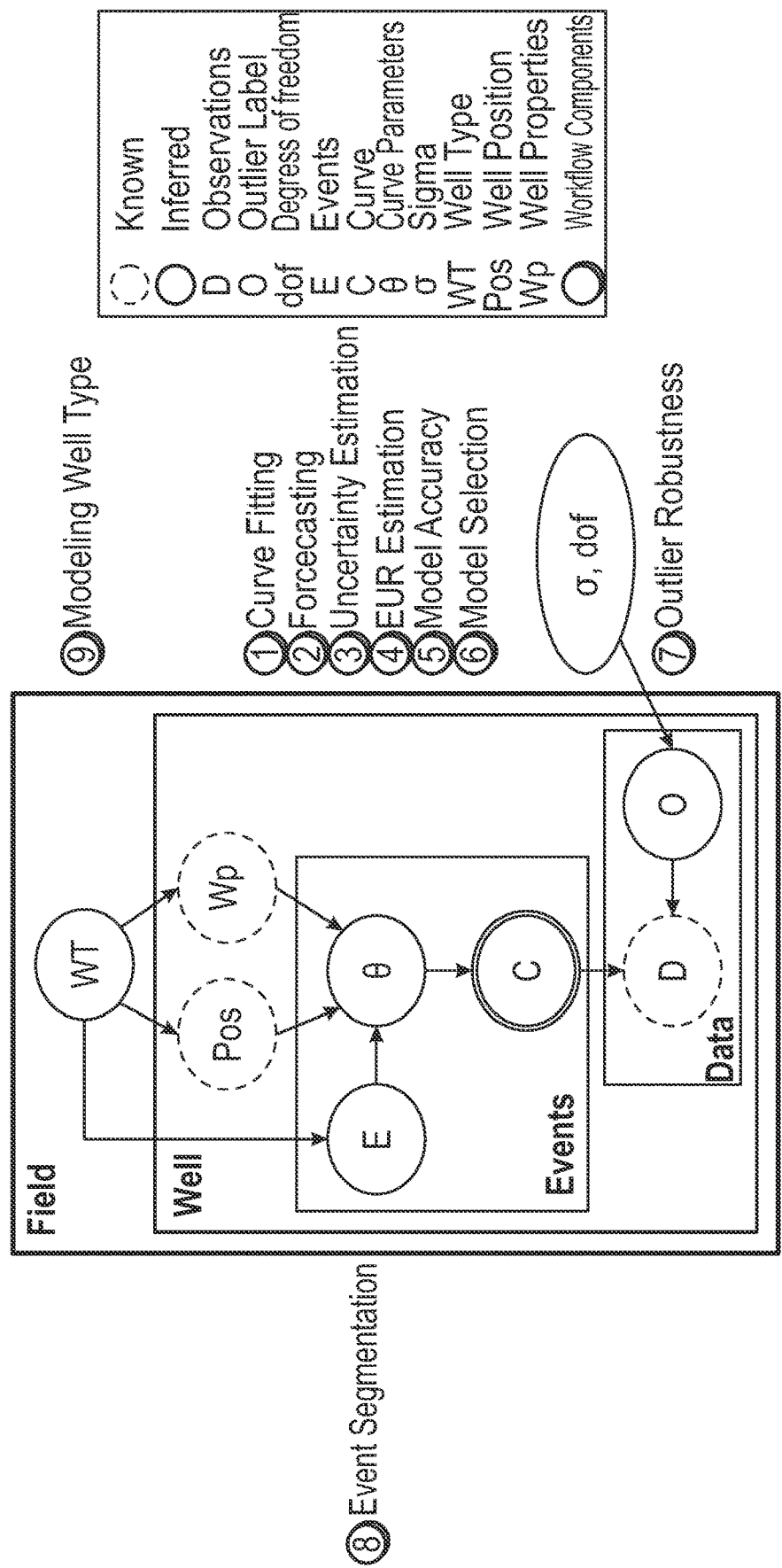
FIG. 13 illustrates a graphical network asset model representing the forecasting plate model per well, according to an embodiment.
Figure 14:
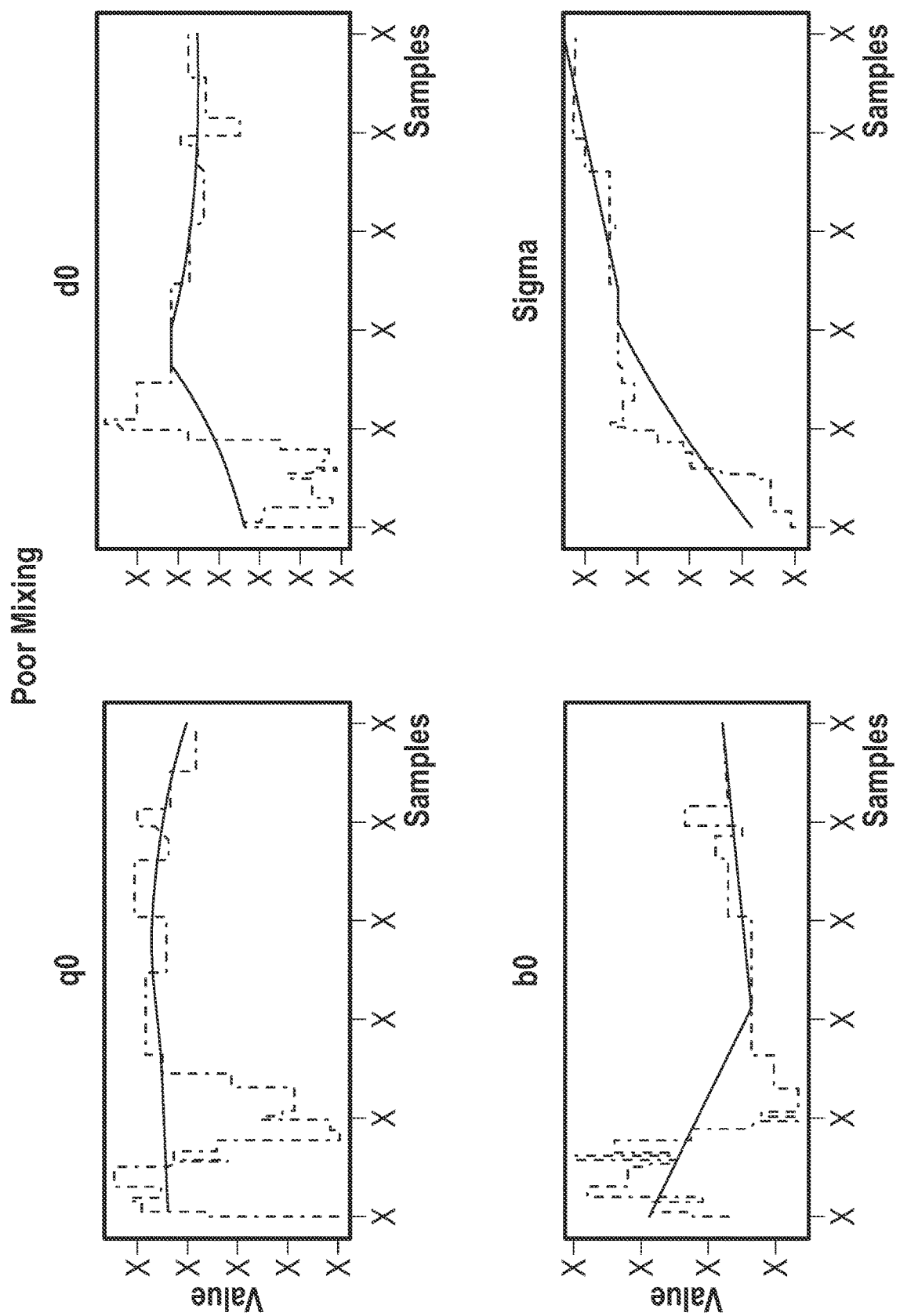
FIG. 14 illustrates plots of prior estimates influence mixing of chains in Markov Chain Monte Carlo analysis, according to an embodiment.
Figure 14:
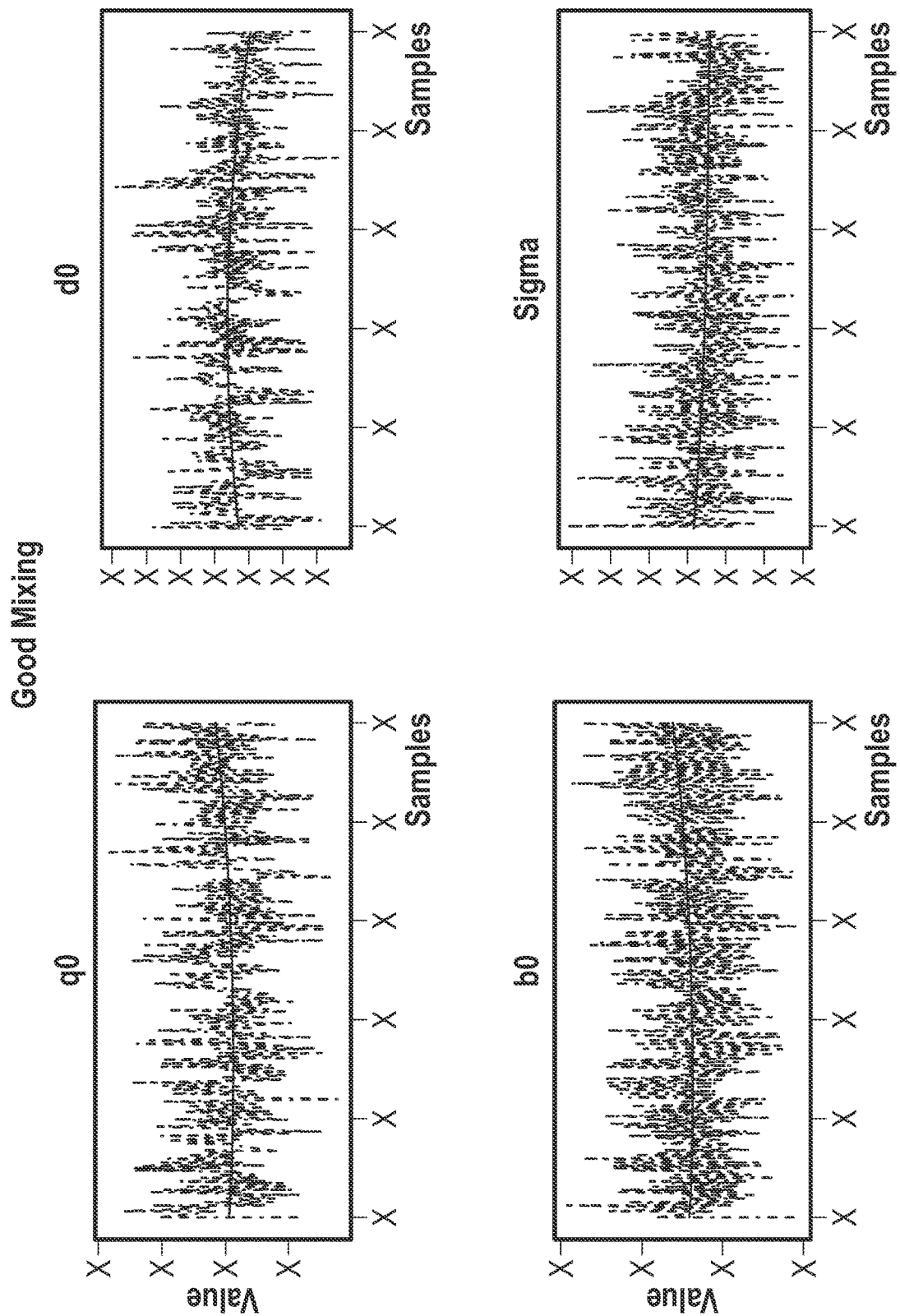

After creating the models for each of the forecasting curves (ARPS, Stretched Exponential, Duong, etc.), automated model selection using information criteria is used for determining the best model, as at 912. FIG. 13 illustrates a graphical network asset model representing the forecasting plate model per well. Such model selection by comparing model accuracy is described, according to an embodiment, above in section 1.f.

Next, the method 900 may proceed to detecting outliers given the data for a well and adding it to the forecasting model, as at 914. Density-based, spatial clustering may be employed, as described above in section 1.b.

The method 900 may then proceed to identifying and segmenting production behavior changing events per well over its life given the data per well, as at 916. Segmenting is described above in section 1.a.

A variation of the model as shown in FIG. 13 includes a robust outlier model using Student t distribution and inferring noise σ and degrees of freedom (dof) in the outlier model. Another variation of the model includes extending the graphical model from well to field to model the well type using well position and well properties and understand their relationship with production potential. As such, a well similarity model may be integrated on top of forecasting model and to illustrate the properties of the complete asset.

In some embodiments, determining the curve fit at 906 may include an inference scheme. The inference scheme may include sub-models for estimating curve parameters. For example, the parameter scheme may involve a fine grid approximation to initialize model parameters, and modeling of priors on parameters for each of the forecasting techniques and the scaling estimates to construct sharp curves. The prior estimates influence mixing of chains in MCMC as shown in Error! Reference source not found. 14. The inference scheme may also include data sampling using MCMC, and high performance implementation by combining results using multiple chains in parallel.

Figure 15:
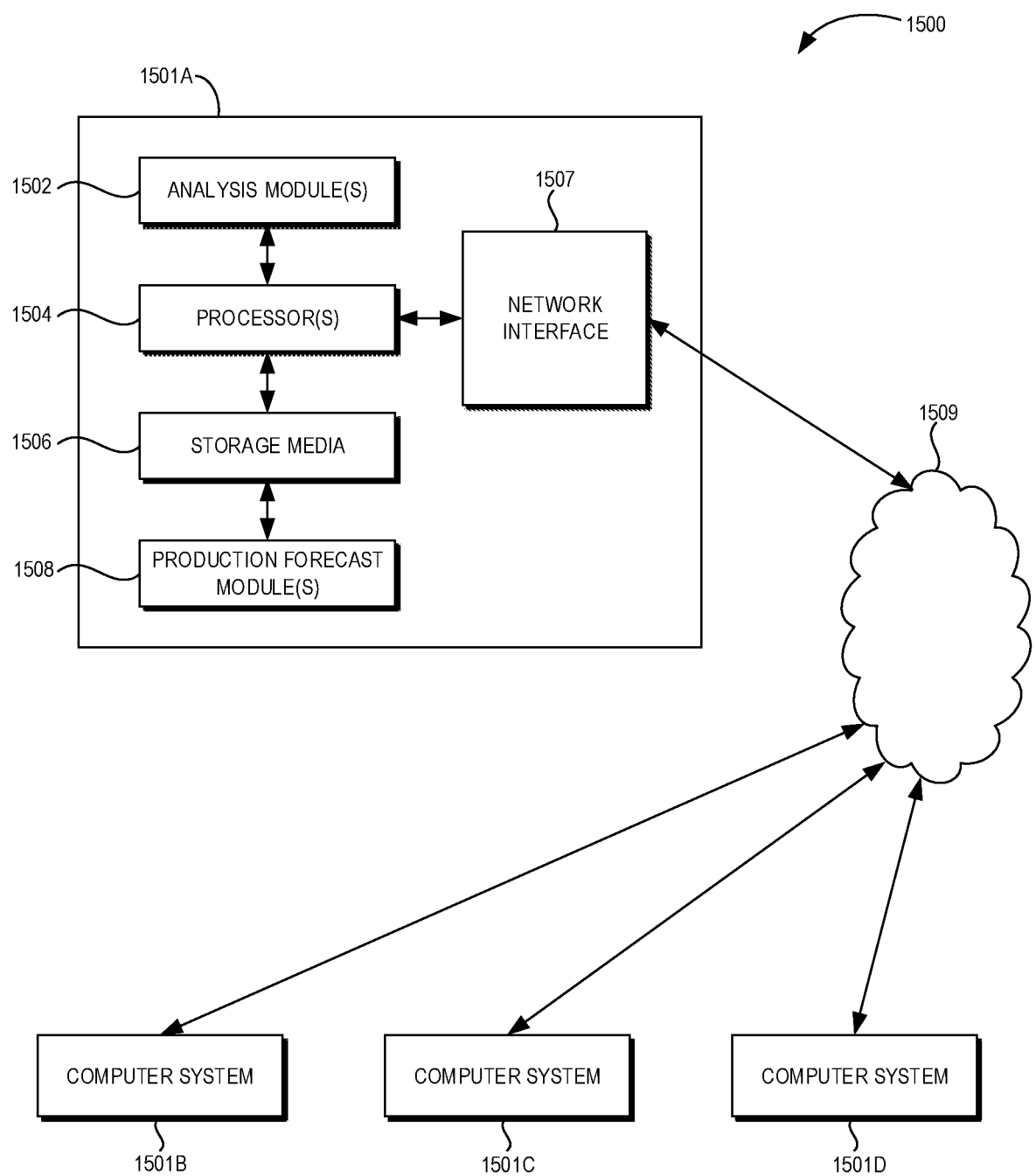
FIG. 15 illustrates an example of a computing system for performing at least a portion of the method, in accordance with some embodiments.

FIG. 15 illustrates an example of such a computing system 1500, in accordance with some embodiments. The computing system 1500 may include a computer or computer system 1501A, which may be an individual computer system 1501A or an arrangement of distributed computer systems. The computer system 1501A includes one or more analysis module(s) 1502 configured to perform various tasks according to some embodiments, such as one or more methods disclosed herein. To perform these various tasks, the analysis module 1502 executes independently, or in coordination with, one or more processors 1504, which is (or are) connected to one or more storage media 1506. The processor(s) 1504 is (or are) also connected to a network interface 1507 to allow the computer system 1501A to communicate over a data network 1509 with one or more additional computer systems and/or computing systems, such as 1501B, 1501C, and/or 1501D (note that computer systems 1501B, 1501C and/or 1501D may or may not share the same architecture as computer system 1501A, and may be located in different physical locations, e.g., computer systems 1501A and 1501B may be located in a processing facility, while in communication with one or more computer systems such as 1501C and/or 1501D that are located in one or more data centers, and/or located in varying countries on different continents).

A processor can include a microprocessor, microcontroller, processor module or subsystem, programmable integrated circuit, programmable gate array, or another control or computing device.

The storage media 1506 can be implemented as one or more computer-readable or machine-readable storage media. Note that while in the example embodiment of FIG. 15 storage media 1506 is depicted as within computer system 1501A, in some embodiments, storage media 1506 may be distributed within and/or across multiple internal and/or external enclosures of computing system 1501A and/or additional computing systems. Storage media 1506 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLU-RAY® disks, or other types of optical storage, or other types of storage devices. Note that the instructions discussed above can be provided on one computer-readable or machine-readable storage medium, or in another embodiment, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some embodiments, computing system 1500 contains one or more production forecast module(s) 1508. In the example of computing system 1500, computer system 1501A includes the production forecast module 1508. In some embodiments, a single production optimization module may be used to perform at least some aspects of one or more embodiments of the method 500. In other embodiments, a plurality of production optimization modules may be used to perform at least some aspects of the method 500.

It should be appreciated that computing system 1500 is one example of a computing system, and that computing system 1500 may have more or fewer components than shown, may combine additional components not depicted in the example embodiment of FIG. 15, and/or computing system 1500 may have a different configuration or arrangement of the components depicted in FIG. 15. The various components shown in FIG. 15 may be implemented in hardware, software, or a combination of both hardware and software, including one or more signal processing and/or application specific integrated circuits.

Further, the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of protection of the invention.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. Moreover, the order in which the elements of the methods are illustrated and described may be re-arranged, and/or two or more elements may occur simultaneously. The embodiments were chosen and described in order to best explain the principals of the invention and its practical applications, to thereby enable others skilled in the art to best utilize the invention and various embodiments with various modifications as are suited to the particular use contemplated.

What is claimed is:

1. A method, comprising:
receiving historical well-production data;
identifying one or more historical behavior-changing events in the historical well- production data;
determining curve parameters after each of the one or more historical behavior-changing events, wherein determining the curve parameters includes accounting for uncertainty;
determining curve fits for the historical well-production data based on the curve parameters using a plurality of models;
calculating accuracy for each of the models based on a comparison of the curve fits to the historical well-production data;
comparing the accuracy for each of the models using an information criteria that accounts for uncertainty;
selecting one of the models based on the comparison of the accuracy;
determining an estimated ultimate recovery (EUR) for a well using at least the selected one of the models;
predicting curve fits for the historical well-production data as if no further historical behavior-changing events are performed;
comparing the curve fits to the predicted curve fits to determine values of production increases provided by the one or more historical behavior-changing events;

weighing the values of the production increases against costs of the one or more historical behavior-changing events; and performing a future behavior-changing event in the well based at least partially upon the EUR, the predicted curve fits, and the weighing, wherein the one or more historical behavior-changing events and the future behavior-changing event comprise a well intervention and/or a workover in the well.

2. The method of claim 1, further comprising determining outliers in the historical well-production data.

3. The method of claim 1, wherein determining the curve fits comprises:
receiving a priori information about the historical well-production data;
determining a posteriori distributions of curve parameters based in part on the a priori information using a Bayesian inference;
determining maximum a posteriori estimates representing a mode of the a posteriori distributions; and
characterizing the distribution of the parameters to approximate a closed form solution for curve-fit parameters using a sampling scheme.

4. The method of claim 1, further comprising:
predicting an effect of two or more types of workovers on the EUR; and
selecting one of the two or more types of workovers to perform in the well based on the predicted effect.

5. The method of claim 1, wherein comparing the accuracy for each of the models comprises calculating a Bayesian Information Criteria (BIC) value for each of the models using:
BIC=klogn−2*LL,
wherein LL is a log-likelihood of the model, k is a number of estimated parameters, and n is a number of data points.

6. The method of claim 1, wherein determining the EUR comprises determining a posterior distribution of EUR values that accounts for uncertainty.

7. The method of claim 1, further comprising:
determining different production signatures from the well due to the one or more historical behavior-changing events;
identifying different classes of behavior-changing events based upon the different production signatures; and
ranking the different classes of behavior-changing events, wherein the future behavior-changing event is also based at least partially upon the ranking.

8. A non-transitory computer-readable medium storing instructions that, when executed by at least one processor of a computing system, cause the computing system to perform operations, the operations comprising:
receiving historical well-production data;
identifying one or more historical behavior-changing events in the historical well-production data;
determining curve parameters after each of the one or more historical behavior-changing events, wherein determining the curve parameters includes accounting for uncertainty;
determining curve fits for the historical well-production data based on the curve parameters using a plurality of models;
calculating accuracy for each of the models based on a comparison of the curve fits to the historical well-production data;
comparing the accuracy for each of the models using an information criteria that accounts for uncertainty;
selecting one of the models based on the comparison of the accuracy;
determining an estimated ultimate recovery (EUR) for a well using at least the selected one of the models;
predicting curve fits for the historical well-production data as if no further historical behavior-changing events are performed;
comparing the curve fits to the predicted curve fits to determine values of production increases provided by the one or more historical behavior-changing events;
weighing the values of the production increases against costs of the one or more historical behavior-changing events;
determining different production signatures from the well due to the one or more historical behavior-changing events;
identifying different classes of behavior-changing events based upon the different production signatures; and
ranking the different classes of behavior-changing events; and
generating or transmitting a signal that instructs or causes performance of a future behavior-changing event in the well based upon the EUR, the predicted curve fits, the weighing, and the ranking, wherein the one or more historical behavior-changing events and the future behavior-changing event comprise a well intervention and/or a workover in the well.

9. The medium of claim 8, wherein the operations further comprise determining outliers in the historical well-production data.

10. The medium of claim 8, wherein determining the curve fits comprises:
receiving a priori information about the historical well-production data;
determining a posteriori distributions of curve parameters based in part on the a priori information using a Bayesian inference;
determining maximum a posteriori estimates representing a mode of the a posteriori distribution; and
characterizing the distribution of the parameters to approximate a closed form solution for curve-fit parameters using a sampling scheme.

11. The medium of claim 8, wherein the operations further comprise:
predicting an effect of two or more types of workovers on the EUR; and
selecting one of the two or more types of workovers to perform in the well based on the predicted effect.

12. The medium of claim 8, wherein comparing the accuracy for each of the models comprises calculating a Bayesian Information Criteria (BIC) value for each of the models using:
BIC=klogn−2*LL,
wherein LL is a log-likelihood of the model, k is a number of estimated parameters, and n is a number of data points.

13. The medium of claim 8, wherein determining the EUR comprises determining a posterior distribution of EUR values that accounts for uncertainty.

14. A computing system, comprising:
one or more processors;
a memory system including one or more non-transitory computer-readable media storing instructions that, when executed by at least one of the one or more processors, cause the computing system to perform operations, the operations comprising:

receiving historical well-production data;

identifying one or more historical behavior-changing events in the historical well-production data;

determining curve parameters after each of the one or more historical behavior-changing events, wherein determining the curve parameters includes accounting for uncertainty;

determining curve fits for the historical well-production data based on the curve parameters using a plurality of models;

calculating accuracy for each of the models based on a comparison of the curve fits to the historical well-production data;

comparing the accuracy for each of the models using an information criteria that accounts for uncertainty;

selecting one of the models based on the comparison of the accuracy;

determining an estimated ultimate recovery (EUR) for a well using at least the selected one of the models;

predicting curve fits for the historical well-production data as if no further historical behavior-changing events are performed;

comparing the curve fits to the predicted curve fits to determine values of production increases provided by the one or more historical behavior-changing events;

weighing the values of the production increases against costs of the one or more historical behavior-changing events;

determining different production signatures from the well due to the one or more historical behavior-changing events;

identifying different classes of behavior-changing events based upon the different production signatures; and ranking the different classes of behavior-changing events; and generating or transmitting a signal that instructs or causes performance of a future behavior-changing event in the well based upon the EUR, the predicted curve fits, the weighing, and the ranking, wherein the one or more historical behavior-changing events and the future behavior-changing event comprise a well intervention and/or a workover in the well.

15. The system of claim 14, wherein the operations further comprise determining outliers in the historical well-production data.

16. The system of claim 14, wherein determining the curve fits comprises:

receiving a priori information about the historical well-production data;

determining a posteriori distributions of curve parameters based in part on the a priori information using a Bayesian inference;

determining maximum a posteriori estimates representing a mode of the a posteriori distribution; and characterizing the distribution of the parameters to approximate a closed form solution for curve-fit parameters using a sampling scheme.

17. The system of claim 14, wherein the operations further comprise:

predicting an effect of two or more types of workovers on the EUR; and selecting one of the two or more types of workovers to perform in the well based on the predicted effect.

18. The system of claim 14, wherein comparing the accuracy for each of the models comprises calculating a Bayesian Information Criteria (BIC) value for each of the models using:

$BIC = k \log n - 2*LL$, wherein LL is a log-likelihood of the model, k is a number of estimated parameters, and n is a number of data points.

* * * * *